(12) United States Patent
Yoo et al.

(10) Patent No.: US 9,127,167 B2
(45) Date of Patent: Sep. 8, 2015

(54) FUNCTIONAL REINFORCING FILLERS MODIFIED WITH ALKENYLALKOXYSILANE AND PREPARING METHOD OF THE SAME

(71) Applicant: KOREA INSTITUTE OF SCIENCE AND TECHNOLOGY, Seoul (KR)

(72) Inventors: Bok Ryul Yoo, Seoul (KR); Joon Soo Han, Gyeonggi-do (KR); Dong Euy Jung, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 0 days.

(21) Appl. No.: 14/030,197

(22) Filed: Sep. 18, 2013

(65) Prior Publication Data

US 2014/0102332 A1   Apr. 17, 2014

Related U.S. Application Data

(63) Continuation-in-part of application No. 13/178,593, filed on Jul. 8, 2011, now Pat. No. 8,563,089.

(30) Foreign Application Priority Data

Apr. 29, 2011   (KR) .................. 10-2011-0041004

(51) Int. Cl.
| | | |
|---|---|---|
| C09C 3/12 | (2006.01) | |
| C08K 9/06 | (2006.01) | |
| C07F 7/18 | (2006.01) | |
| C08G 77/04 | (2006.01) | |
| C08K 5/5425 | (2006.01) | |
| C09C 1/36 | (2006.01) | |
| C09C 1/40 | (2006.01) | |
| C09C 1/04 | (2006.01) | |
| C09C 1/30 | (2006.01) | |

(52) U.S. Cl.
CPC ... *C09C 3/12* (2013.01); *C07F 7/18* (2013.01); *C08G 77/045* (2013.01); *C08K 5/5425* (2013.01); *C08K 9/06* (2013.01); *C09C 1/043* (2013.01); *C09C 1/30* (2013.01); *C09C 1/3607* (2013.01); *C09C 1/407* (2013.01)

(58) Field of Classification Search
None
See application file for complete search history.

(56) References Cited

U.S. PATENT DOCUMENTS

| | | | |
|---|---|---|---|
| 3,842,111 A | 10/1974 | Meyer-Simon | |
| 4,384,132 A | 5/1983 | Schwarz et al. | |
| 4,507,490 A | 3/1985 | Panster et al. | |
| 5,227,425 A | 7/1993 | Rauline | |
| 6,797,762 B2 | 9/2004 | Agostini et al. | |
| 7,488,768 B2 | 2/2009 | Tardivat et al. | |
| 7,846,993 B2 * | 12/2010 | Ko et al. | 523/212 |
| 8,003,724 B2 | 8/2011 | Hahn et al. | |
| 8,097,674 B2 | 1/2012 | Hergenrother et al. | |
| 8,129,458 B2 | 3/2012 | Yoo et al. | |
| 2003/0019554 A1 | 1/2003 | Agostini et al. | |
| 2005/0176852 A1 | 8/2005 | Okel et al. | |
| 2009/0068123 A1 | 3/2009 | Takei et al. | |

FOREIGN PATENT DOCUMENTS

EP   0501227 A1   9/1992

OTHER PUBLICATIONS web page http://chemistry.about.com/od/workedchemistryproblems/a/phweakacid.htm.*
S. Wolff, et al. "Reinforcing and Vulcanization Effects of Silane Si 69 in Silica-Filled Compounds", Kautsch, Gummi, Kunstst. 34, pp. 280-284, 1981 (Exact date not given nor found).
S.D. Korkin, et al; "Phenylsilanetriol—synthesis, stability, and reactivity", Journal of Organometallic Chemistry, vol. 686, pp. 313-320, Nov. 2003.
Hatsuo Ishida, et al; "Molecular Organization of the Coupling Agent Interphase of Fiber-Glass Reinforced Plastics", Journal of Polymer Science: Polymer Physics Edition, vol. 17, pp. 1807-1813; Oct. 1979.
Peter jutzi, et al; "Synthesis, Derivatization, and Structure of the Silanetriol [C5H4(SiMe3)]Si(OH)3: Unique Hydrogen Bonding in a Highly Symmetrical Tubular Assembly", Organometallics, vol. 16, pp. 5377-5380; Publication Date (Web): Nov. 25, 1997.
USPTO NFOA dated Feb. 25, 2013 in connection with U.S. Appl. No. 13/178,593.
USPTO NOA mailed Jun. 20, 2013 in connection with U.S. Appl. No. 13/178,593.

* cited by examiner

*Primary Examiner* — Marc Zimmer
(74) *Attorney, Agent, or Firm* — Ladas & Parry LLP

(57) ABSTRACT

Disclosed are a functional reinforcing filler including inorganic particles surface-modified with an alkenylsilanol obtained by hydrolyzing an alkenylalkoxysilane compound, and a method for preparing the same. Since the disclosed functional reinforcing filler has a functional group having a double bond, it has good reactivity for styrene-butadiene rubber and sulfur. Thus, when used as a functional reinforcing filler in the manufacture of rubber, it allows improvement of physical properties through adjustment of the addition amount of sulfur without additional use of the coupling agent. In addition, because of superior hydrolysis reactivity, the problem of alcohol can be solved and a rubber mixture with long scorch time can be prepared. In particular, when the functional reinforcing filler of the present invention is used in the manufacture of tires, improvement in modulus, tensile strength, rotational resistance and wet traction performance can be expected.

11 Claims, 1 Drawing Sheet

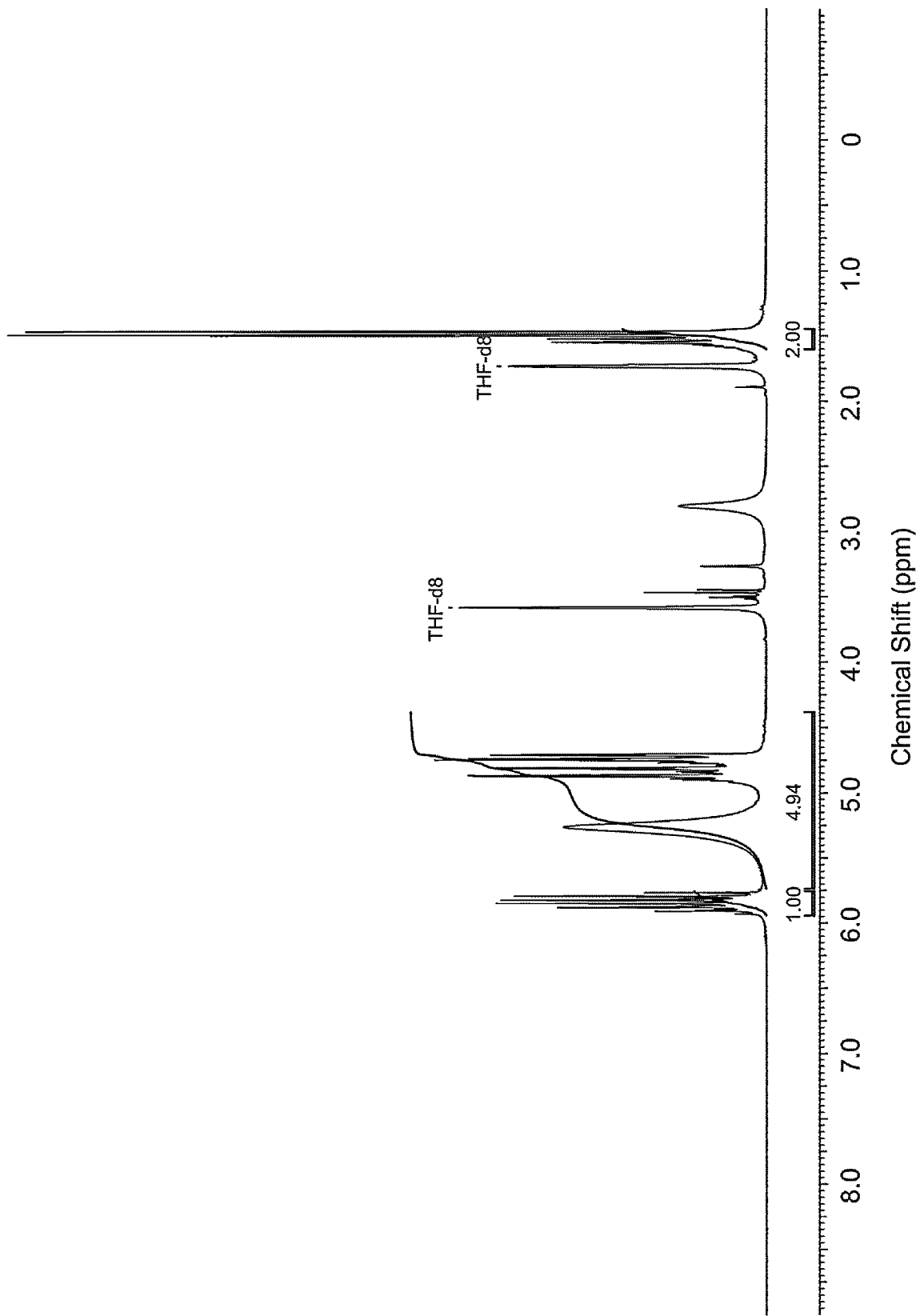

FUNCTIONAL REINFORCING FILLERS MODIFIED WITH ALKENYLALKOXYSILANE AND PREPARING METHOD OF THE SAME

CROSS-REFERENCE TO RELATED APPLICATIONS

This application claims priority under 35 U.S.C. §119 to Korean Patent Application No. 10-2011-0041004 filed on Jun. 15, 2011, in the Korean Intellectual Property Office, the disclosure of which is incorporated herein by reference in its entirety.

BACKGROUND (a) Technical Field

The present invention relates to a functional reinforcing filler including inorganic particles surface-modified with an alkenylsilanol obtained from hydrolysis of an alkenylalkoxysilane compound.

(b) Background Art

Since the mid-20th century, silanes having organic functional groups have been widely used to enhance adhesion between silica and polymers or to improve compatibility. But, it is reported that a silica-filled rubber composition does not have the desired reinforcing effect and an excellent improvement in physical properties is attained when a sulfur-containing coupling agent such as 3-mercaptopropyltrimethoxysilane (MPTMS) is used [U.S. Pat. No. 0,176,852 A1]. However, the mercaptoalkyltrialkoxysilane coupling agent has offensive odor and, when it is mixed with a polymer composition, processability is degraded since the prevulcanization time is greatly reduced due to the highly reactive thiol (—SH) group.

In the early 1970s, bis(alkoxysilylalkyl)polysulfides[(RO)$_3$SiCH$_2$CH$_2$CH$_2$SxCH$_2$CH$_2$CH$_2$Si(OR)$_3$] were developed [U.S. Pat. No. 3,842,111, U.S. Pat. No. 4,384,132, U.S. Pat. No. 4,507,490]. And, in the early 1990s, Michelin announced the "green tires" using bis(triethoxysilylpropyl) tetrasulfide (TESPT) [Eur. Patent EP 0501227, U.S. Pat. No. 5,227,425]. Since then, TESPT has been frequently used as filler along with silica in order to improve the physical properties of a rubber composition. However, TESPT is restricted in temperature when mixing with a rubber composition. For instance, when it is mixed with a rubber composition at high temperature, prevulcanization of the rubber mixture occurs because of irreversible thermal cracking of the polysulfane groups. And, when the mixing is performed at low temperature, the alkoxy group of TESPT may not be completely hydrolyzed. According to Wolff, S., complete hydrolysis of TESPT is difficult to be attained at low temperature because of steric hindrance [Wolff, S. Kautsch. Cummi, Kunstst 1981, 34, 280]. As a result, the residual alkoxy group exists in the molecule and hydrolysis occurs continuously even after mixing with the rubber composition. It decreases the life span of the rubber mixture as it is released as alcohol from inside the rubber matrix.

Thus, highly dispersible silica capable of minimizing the release of alcohol and enhancing the dispersibility of silica is consistently developed by silica manufacturers [U.S. Pat. No. 044,037]. However, use of TESPT cannot be free from the release of alcohol. At present, most of silica-containing rubbers use TESPT or MPTMS, and it is quite uncommon to use a silane having a sulfur-free organic functional group, which allows less improvement in rubber properties, in a rubber mixture for a tire.

It is known that when an alkenylalkoxysilane having a sulfur-free organic functional group is mixed with a rubber together with silica, rubber properties can be improved by using a catalyst such as butyllithium or peroxide [U.S. Pat. No. 0,019,554 A1]. However, in that case, coupling tends to occur with the silane coupling agent rather than the coupling between silica and rubber due to hydrolysis of the chlorine or alkoxy group of the silane, thus resulting in the formation of polysiloxane. This leads to insufficient improvement in the properties of the tire composite and inevitably leads to unfavorable processability and economic loss because of the need of additional use of additives in the manufacture of rubber for tires.

In contrast, alkenylsilane, which is commonly used in the manufacture of a rubber mixture, allows a long prevulcanization time when mixing with a rubber composition and the mixing temperature is not particularly restricted. However, liquid alkenylsilanes, especially vinylsilane and allylsilane, have storage problems because of fast hydrolysis. During mixing with the rubber mixture, they are hydrolyzed quickly, leading to fast condensation with the coupling agent rather than the silica-coupling agent-rubber coupling. Also, a larger amount of sulfur is required as compared to when a sulfur-containing coupling agent, e.g. MPTMS or TESPT, is used. That is to say, since the coupling agent is sulfur-free, solid sulfur or peroxide has to be added. Unless the rubber mixture is mixed homogeneously, the desired improvement in physical properties cannot be attained.

In general, silanetriol is synthesized by hydrolyzing chlorosilane or alkoxysilane. As a typical example of using chlorosilane, Jutzi et al. reported synthesis of (1-trimethylsilylcyclopenta-2,-4-dienyl)silanetriol with a yield of 98% by dissolving (1-trimethylsilylcyclopenta-2,-4-dienyl)trichlorosilane, a chlorosilane with large steric hindrance, in ethyl ether, slowly adding an aniline aqueous solution and stirring at 0° C. for 3 hours, removing the resulting aniline salt through filtration and then removing ethyl ether under reduced pressure [*Organometallics* 1997, 16, 5377]. However, this method involves a complicated process of removing a large amount of salts and is limited in that it is applicable only to silanes having substituents with large steric hindrance. As a typical example of using alkoxysilane, Ishida et al. obtained cyclohexylsilanetriol by mixing cyclohexyltrimethoxysilane in an aqueous solution of acetic acid and stirring for 2 hours at room temperature [*J. Polym. Sci.* 1979, 17, 1807]. In addition, Korkin et al. reported that they obtained phenylsilanetriol with a yield of 68% by adding phenyltrimethoxysilane dropwise to an acetic acid aqueous solution, stirring for 4 hours while maintaining temperature at 5-10° C. and removing impurities from the resulting white solid through filtration [*J. Organomet. Chem.* 2003, 686, 313]. However, the method of using alkoxysilane is limited in that the resultant silanetriol should be insoluble in water.

SUMMARY

The inventors of the present invention have worked to solve the aforesaid problems of the existing art. As a result, they have found out that, by chemically treating the surface of inorganic particles with a sulfur-free alkenylalkoxysilane compound instead of using bis(triethoxysilylpropyl)tetrasulfide (TESPT) or 3-mercaptopropyltrimethoxysilane (MPTMS), a hydrophobic, highly dispersible, a functional reinforcing filler having superior crosslinking reactivity and being easily miscible with rubber can be prepared.

The present invention is directed to providing a functional reinforcing filler and a method for preparing the same.

In one general aspect, the present invention provides a functional reinforcing filler including inorganic particles surface-modified with an alkenylsilanol solution obtained by hydrolyzing an alkenylalkoxysilane compound represented by Chemical Formula 1:

$$R-SiX^1X^2X^3 \quad (1)$$

wherein R is $C_2$-$C_{18}$ alkenyl or $C_5$-$C_{18}$ cycloalkenyl, and each of $X^1$, $X^2$ and $X^3$, which are the same or different, is $C_1$-$C_{18}$ alkyl, $C_1$-$C_{18}$ alkoxy, $C_6$-$C_{18}$ aryl or $C_6$-$C_{18}$ aromatic alkoxy, with the proviso that at least one of $X^1$, $X^2$ and $X^3$ is $C_1$-$C_{18}$ alkoxy or $C_6$-$C_{18}$ aromatic alkoxy.

In another general aspect, the present invention provides a method for preparing a functional reinforcing filler, including: preparing an alkenylsilanol solution by hydrolyzing the alkenylalkoxysilane compound represented by Chemical Formula 1; preparing a suspension by mixing the alkenylsilanol solution with inorganic particles in one or more solvent selected from alcohol and water; preparing molecular film coated inorganic particles by removing the solvent from the suspension through evaporation; and heating the molecular film coated inorganic particles to induce dehydration condensation.

In another general aspect, the present invention provides a method for preparing a functional reinforcing filler, including: preparing a suspension by mixing the alkenylalkoxysilane compound represented by Chemical Formula 1 with inorganic particles in one or more solvent selected from alcohol and water; removing the solvent from the suspension through evaporation; and heating the inorganic particles to induce dehydration condensation and thereby modifying the surface of the inorganic particles.

The above and other aspects and features of the present invention will be described infra.

BRIEF DESCRIPTION OF THE DRAWINGS

FIG. 1 shows a $^1$H NMR spectrum of the allylsilanetriol synthesized in Synthesis Example 1.

DETAILED DESCRIPTION

Hereinafter, reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention provides a functional reinforcing filler comprising inorganic particles surface-modified with an alkenylsilanol solution obtained by hydrolyzing an alkenylalkoxysilane compound represented by Chemical Formula 1:

$$R-SiX^1X^2X^3 \quad (1)$$

wherein R is $C_2$-$C_{18}$ alkenyl or $C_5$-$C_{18}$ cycloalkenyl, and each of $X^1$, $X^2$ and $X^3$, which are the same or different, is $C_1$-$C_{18}$ alkyl, $C_1$-$C_{18}$ alkoxy, $C_6$-$C_{18}$ aryl or $C_6$-$C_{18}$ aromatic alkoxy, with the proviso that at least one of $X^1$, $X^2$ and $X^3$ is $C_1$-$C_{18}$ alkoxy or $C_6$-$C_{18}$ aromatic alkoxy.

R is $C_2$-$C_{18}$ alkenyl or $C_5$-$C_{18}$ cycloalkenyl. The number of carbon atoms of R may be in the aforesaid range since it is not easy to prepare an alkenyl group having more than 18 carbon atoms and the processing time may increase due to slow hydrolysis. More specifically, it may be $C_2$-$C_{10}$ alkenyl.

Each of $X^1$, $X^2$ and $X^3$ is $C_1$-$C_{18}$ alkyl, $C_1$-$C_{18}$ alkoxy, $C_6$-$C_{18}$ aryl or $C_6$-$C_{18}$ aromatic alkoxy, with the proviso that at least one of $X^1$, $X^2$ and $X^3$ is $C_1$-$C_{18}$ alkoxy or $C_6$-$C_{18}$ aromatic alkoxy to allow conversion into an alkenylsilanol via hydrolysis.

Particularly, the alkenylalkoxysilane compound may be one or more compound selected from vinyltrimethoxysilane (VTMS), allyltrimethoxysilane (ATMS), 5-hexenyltrimethoxysilane (HTMS), 7-octenyltrimethoxysilane (OTMS), (bicyclo[2.2.1]hept-5-en-2-yl)trimethoxysilane (BCHTMS), vinyltriethoxysilane (VTES), allyltriethoxysilane (ATES), 5-hexenyltriethoxysilane (HTES), 7-octenyltriethoxysilane (OTES) and (bicyclo[2.2.1]hept-5-en-2-yl)triethoxysilane (BCHTES). Most specifically, allyltrialkoxysilane may be used.

The inorganic particles may be one or more selected from silica, mica, talc, titanium oxide, zirconium oxide, tin oxide, iron oxide and zinc oxide, although not being limited thereto. Specifically, one or more selected from silica and mica may be used. And, the inorganic particles may have an average particle diameter of 5 nm to 100 μm. When the average particle diameter is smaller than 5 nm, the cost is too high. And, when it exceeds 100 μm, the performance of the elastomer as the reinforcing filler may be degraded. Hence, the average particle diameter may be within the aforesaid range. And, the inorganic particles may have a BET surface area of 50 to 1,000 m$^2$/g. The silica may be one or more selected from precipitated silica and colloidal silica. More specifically, one or more selected from Zeosil (Rhodia), Hi-Sil (PPG Industries) and VN (Evonik) may be used. The precipitated silica may be prepared by various methods known in the art. As a specific example, it may be prepared from a solution of sodium silicate by acid precipitation.

Hereinafter, a method for preparing the functional reinforcing filler of the present invention will be described in detail.

[Preparation Method]

The functional reinforcing filler of the present invention comprising inorganic particles surface-modified with an alkenylsilanol solution obtained by hydrolyzing an alkenylalkoxysilane compound represented by Chemical Formula 1 may be prepared by the following two preparation methods:

$$R-SiX^1X^2X^3 \quad (1)$$

wherein R is $C_2$-$C_{18}$ alkenyl or $C_5$-$C_{18}$ cycloalkenyl, and each of $X^1$, $X^2$ and $X^3$, which are the same or different, is $C_1$-$C_{18}$ alkyl, $C_1$-$C_{18}$ alkoxy, $C_6$-$C_{18}$ aryl or $C_6$-$C_{18}$ aromatic alkoxy, with the proviso that at least one of $X^1$, $X^2$ and $X^3$ is $C_1$-$C_{18}$ alkoxy or $C_6$-$C_{18}$ aromatic alkoxy.

[Preparation Method 1]

The functional reinforcing filler of the present invention may be prepared from a process comprising: a first step of preparing an alkenylsilanol solution by hydrolyzing the alkenylalkoxysilane compound represented by Chemical Formula 1; a second step of preparing a suspension by mixing the alkenylsilanol solution with inorganic particles in one or more solvent selected from alcohol and water; a third step of preparing molecular film coated inorganic particles by removing the solvent from the suspension through evaporation; and a fourth step of heating the molecular film coated inorganic particles to induce dehydration condensation.

In the first step, an organic acid that can be evaporated relatively easily or do not require neutralization may be used as an acid to hydrolyze the alkenylalkoxysilane compound. Specific examples include carboxylic acids such as acetic acid, formic acid, butyric acid, palmitic acid, oxalic acid, tartaric acid, etc., ascorbic acid, uric acid, or the like, but are not limited thereto. The hydrolysis of the alkenylalkoxysilane compound may be performed at 0 to 100° C., more specifically at 10 to 80° C. The reaction temperature may be different depending on the kind of reactants, e.g., organometallic compounds, acids and fillers, and solvents. And, the hydrolysis may be performed at pH 2.5-5.0. When the pH is below 2.5, formation of polysiloxane may be accelerated due as the alkenylalkoxysilane is hydrolyzed quickly, thereby resulting in reduced reactivity with the surface of the inorganic particles. And, when the pH exceeds 5.0, alcohol may be released during mixing with the rubber composition because the hydrolysis occurs too slowly. Hence, the aforesaid pH range may be preferred.

In the second step, the solvent used in the suspension may be one or more solvent selected from alcohol and water. The alcohol may be $C_1$-$C_{10}$ alcohol. Specifically, it may be selected from methanol, ethanol, propyl alcohol, butanol, pentanol, hexanol or phenol.

When preparing the suspension, a sulfur-containing coupling agent may be additionally added. Specifically, the coupling agent may be a sulfur-containing compound selected from bis[(trimethoxysilyl)propyl]tetrasulfide (TMSPT), bis[(triethoxysilyl)propyl]tetrasulfide (TESPT), 3-mercaptopropyltrimethoxysilane (MPTMS) and 3-mercaptopropyltriethoxysilane (MPTES).

In the third step, as the solvent included in the suspension evaporates, the silanol (Si—OH) group of the hydrolyzed alkenylsilanol is coated on the surface of the inorganic particles via hydrogen bonding with the hydroxyl (M-OH) groups on the surface of the inorganic particles, thus forming a molecular film. Later, when the molecular film is heated, M-O—Si covalent bonding is formed via dehydration condensation. Since the solvent is removed by evaporation, an additional neutralization or filtration process may be unnecessary. In this process, low-boiling-point alcohol may be removed.

In the fourth step, the dehydration condensation may be performed at 100° C. or higher, specifically at 100-150° C., under a pressure of 1 to 20 mmHg.

The alkenylalkoxysilane compound represented by Chemical Formula 1 may be used in an amount of 1 to 20 parts by weight, specifically 3 to 15 parts by weight, more specifically 5 to 15 parts by weight, based on 100 parts by weight of the inorganic particles.

[Preparation Method 2]

Also, the functional reinforcing filler of the present invention may be prepared from a process comprising: preparing a suspension by mixing the alkenylalkoxysilane compound represented by Chemical Formula 1 with inorganic particles in one or more solvent selected from alcohol and water under an acidic condition; removing the solvent from the suspension through evaporation; and heating the inorganic particles to induce dehydration condensation and thereby modifying the surface of the inorganic particles:

In the preparation method 2, unlike in the preparation method 1, the surface of the inorganic particles is chemically modified while the alkenylalkoxysilane compound is hydrolyzed. However, the two preparation methods have many things in common in that 1) the coated inorganic particles are dehydration condensed after the alcohol and water are removed by evaporation, 2) the prepared hydrophobic, highly dispersible functional reinforcing filler does not release the alcohol component, and 3) the same reactants are used. In the preparation method 2, like in the preparation method 1, a molecular film is formed on the surface of the inorganic particles via hydrogen bonding between the silanol (Si—OH) group of the hydrolyzed alkenylsilanol and the hydroxyl (M-OH) group on the surface of the inorganic particles as the alcohol and water are evaporated. When the molecular film is heated, M-O—Si covalent bonding is formed via dehydration condensation. Since the alcohol and water are removed by evaporation, an additional neutralization or filtration process may be unnecessary. In this process, low-boiling-point alcohol may be removed.

The alkenylalkoxysilane compound represented by Chemical Formula 1 may be used in an amount of 1 to 20 parts by weight, specifically 3 to 15 parts by weight, more specifically 5 to 15 parts by weight, based on 100 parts by weight of the inorganic particles.

The acidic condition may be pH 2.5-5.0. Under this condition, the alkenylalkoxysilane compound is hydrolyzed to give a clear solution. When the pH is below 2.5, formation of polysiloxane may be accelerated due as the alkenylalkoxysilane is hydrolyzed quickly, thereby resulting in reduced reactivity with the surface of the inorganic particles. And, when the pH exceeds 5.0, alcohol may be released during mixing with the rubber composition because the hydrolysis occurs too slowly. Hence, the aforesaid pH range may be preferred. And, an organic acid that can be evaporated relatively easily or do not require neutralization may be used as an acid to prepare the acidic condition. Specific examples include carboxylic acids such as acetic acid, formic acid, butyric acid, palmitic acid, oxalic acid, tartaric acid, etc., ascorbic acid, uric acid, or the like, but are not limited thereto.

The alcohol may be $C_1$-$C_{10}$ alcohol. Specifically, it may be selected from methanol, ethanol, propyl alcohol, butanol, pentanol, hexanol or phenol.

When mixing the alkenylalkoxysilane compound with the inorganic particles, the alcohol and water, a sulfur-containing coupling agent may be additionally added. Specifically, the coupling agent may be a sulfur-containing compound selected from bis[(trimethoxysilyl)propyl]tetrasulfide (TMSPT), bis[(triethoxysilyl)propyl]tetrasulfide (TESPT), 3-mercaptopropyltrimethoxysilane (MPTMS) and 3-mercaptopropyltriethoxysilane (MPTES).

The highly dispersible functional reinforcing filler of the present invention prepared by the preparation method 1 or 2 does not emit volatile organic compounds (VOCs) because the alkenylalkoxysilane is hydrolyzed. The functional reinforcing filler of the present invention contains 0.1 wt % or more, specifically 0.1 to 20 wt %, of carbon based on the total weight of the reinforcing filler.

Hereinafter, a rubber composition comprising the hydrophobic, highly dispersible functional reinforcing filler of the present invention will be described.

[Rubber Composition]

The present invention is also directed to providing a rubber composition comprising the highly dispersible functional reinforcing filler. To describe in more detail, the rubber composition of the present invention comprises an elastomer as well as the hydrophobic, highly dispersible functional reinforcing filler. It may further comprise one or more additive selected from an accelerator and a retardant.

In the rubber composition, the hydrophobic, highly dispersible functional reinforcing filler may be used in an amount of 10 to 200 parts by weight, more specifically 20 to 150 parts by weight, based on 100 parts by weight of the elastomer.

The elastomer may be a thermoplastic or thermosetting elastomer. Specifically, one or more selected from a homopolymer comprising conjugated diene monomers and a copolymer comprising a conjugated diene monomer, a monovinyl aromatic monomer and a triene monomer may be used.

The elastomer may further comprise an organic rubber. The organic rubber may comprise one or more selected from: a natural rubber (formed from homopolymerization of butadiene or its homologues or derivatives); 1,4-polyisoprene, 3,4-polyisoprene, trans-1,4-polybutadiene, cis-1,4-polybutadiene or 1,2-polybutadiene; one or more ethylene-based unsaturated copolymeric monomer comprising butadiene and its homologues or derivatives; a butadiene-styrene copolymer using a butadiene isomer; polymers of isoprene, styrene and butadiene and various terpolymers thereof; an acrylonitrile-based copolymer and terpolymer rubber composition; and an isobutylene-based rubber.

Also, the elastomer may further comprise alkyd resin, natural oil, oil-modified alkyd resin, nylon, epoxide, thermoplastic polyester, unsaturated polyester, polycarbonate, or the like. More specifically, polyethylene, polypropylene, polybutylene, polystyrene, ethylene-propylene copolymer or terpolymer, polyoxymethylene and its copolymer, polyurethane, nitrocellulose, phenol resin, polysulfide rubber, vinyl butyrate, vinyl chloride, vinyl acetate, cellulose acetate and butyrate, viscose rayon, cellulose, ethylene copolymer, wax, shellac, organic rubber, etc. may be used. However, the present invention is not limited thereto.

A non-limiting example of preparing a rubber composition using the functional reinforcing filler of the present invention is as follows.

A vulcanized rubber composition may be prepared by a process comprising: a step of mixing a curable elastomer with the hydrophobic, highly dispersible functional reinforcing filler, an accelerator and a retardant to form a vulcanizable elastomer composition; and a step of curing the vulcanizable elastomer composition by adding a curing agent.

The accelerator may be one or more selected from benzothiazole, benzothiazole sulfenamide, dithiocarbamate, thiopholine, thiourea, xanthate, thiuram sulfide, amine and dithiophosphate.

More specifically, the accelerator may comprise one or more selected from:

one or more benzothiazole selected from 2-mercaptobenzothiazole, zinc 2-mercaptobenzothiazole, 2,2'-dithiobisbenzothiazole, 2-morpholinothiobenzothiazole, 2-(4-morpholinodithio)benzothiazole, 2-(4-morpholinothio)benzothiazole, 2-(4-morpholinothio)-5-methylbenzothiazole, 2-(4-morpholinothio)-5-chlorobenzothiazole, 2-(2,6-dimethyl-4-morpholinothio)-benzothiazole, 2-(3,6-dimethyl-4-morpholinothio)benzothiazole, 2,2'-dibenzothiazole disulfide and 2-mercaptobenzothiazyl disulfide);

one or more benzothiazole sulfenamide selected from N-cyclohexyl-2-benzothiazole sulfenamide, N,N'-dicyclohexyl-2-benzothiazole sulfenamide, N,N-diethyl-2benzothiazole sulfenamide, N-t-butyl-2-benzothiazole sulfenamide, N,N-diisopropyl-2-benzothiazole sulfenamide, N-oxydiethylene-2-benzothiazole sulfenamide and N-oxydiethylene thiocarbamyl-N-oxydiethylene sulfenamide;

one or more dithiocarbamate selected from cadmium diethyldithiocarbamate, lead diamyldithiocarbamate, lead dimethyldithiocarbamate, zinc dimethyldithiocarbamate, zinc diethyldithiocarbamate, zinc diamyldithiocarbamate, zinc di-n-butyldithiocarbamate, zinc dimethylpentamethylene dithiocarbamate, bismuth dimethyldithiocarbamate, copper dimethyldithiocarbamate, selenium diethyldithiocarbamate, selenium dimethyldithiocarbamate, tellurium diethyldithiocarbamate, piperidinium pentamethylene dithiocarbamate, 2-benzothiazole-N,N-diethyldithiocarbamate and dimethyl ammonium dimethyldithiocarbamate;

one or more thiopholine selected from 4-mercaptomorpholine, 4-mercapto-2,6-dimethylmorpholine, 4,4'-dithiomorpholine, 4-[(4-morpholinylthio)thixomethyl]morpholine, 2,6-dimethylmorpholine disulfide, methylmorpholine disulfide, propyl 2,6-dimethyl morpholine disulfide, alkyl morpholine disulfide and phenyl morpholine disulfide;

one or more thiourea selected from trimethylthiourea, 1,3-dibutylthiourea, N,N'dibutylthiourea, 1,3-diethylthiourea, dimethylethylthiourea, diphenylthiourea and tetramethylthiourea;

one or more xanthate selected from sodium isopropylxanthate, zinc isopropylxanthate and zinc dibutylxanthate;

one or more thiuram sulfide selected from tetramethylthiuram monosulfide, tetramethylthiuram disulfide, tetraethylthiuram disulfide, tetrabutylthiuram disulfide, dipentamethylenethiuram tetrasulfide, tetrabenzylthiuram disulfide, dimethyldiphenylthiuram disulfide and dipentamethylenethiuram monosulfide;

one or more amine selected from cyclohexylethylamine, dibutylamine, heptaldehyde-aniline condensate, acetaldehyde-aniline condensate and guanidine, e.g., N,N'-diphenylguanidine, N,N'-di-o-tolylguanidine, o-tolylbiguanidine, N,N',N"-triphenylguanidine and diarylguanidine; and dithiophosphate.

And, the retardant may be one or more amine selected from N-(cyclohexylthio)phthalimide, phthalic anhydride, benzoic acid, salicylic acid, stearic acid, N-nitrosodiphenylamine, sodium acetate, aromatic sulfonamide, dioctyl phthalate and magnesium oxide. More specifically, the retardant may be one or more amine selected from N-(cyclohexylthio)phthalimide, phthalic anhydride and aromatic sulfenamide.

In addition, the rubber composition may further comprise sulfur in order to improve physical properties. Specifically, sulfur may be added in an amount of 0.1 to 10 parts by weight, more specifically 1 to 5 parts by weight.

Rubber prepared using the rubber composition including the functional reinforcing filler of the present invention may have high tan δ at 0° C. and low tan δ at 60° C. Furthermore, the hydrophobic, highly dispersible functional reinforcing filler of the present invention is capable of improving the processability and physical properties of rubber. The rubber prepared using the hydrophobic, highly dispersible functional reinforcing filler of the present invention may have a scorch time exceeding 14 minutes and a curing time less than 30 minutes (ASTM D5289-95). The compounded product may have a 300% modulus of at least 5.0 MPa (ASTM D412-98a). The hydrophobic, highly dispersible functional reinforcing filler of the present invention may be applied to the manufacture of a variety of rubber products, e.g., automotive drive-belts, engine mounts, V-belts, conveyor belts, roller coatings, tires, components of tire (vehicle tire treads, subtreads, carcases, sidewalls, belt wedges, bead fillers and wire skim coats), shoe sole materials, packing rings, wire and cable sheaths, hoses, gaskets, sealing materials, or the like, so that the rubber products may have excellent tensile properties and dynamic properties.

The present invention presents the structure of a silanepolyol that can be used as an inorganic oxide surface modifier regardless of solubility in water and a method for synthesizing same.

The present invention provides a terminal alkenylsilanepolyol derivative represented by Chemical Formula 2 used as an inorganic oxide surface modifier, which is obtained by hydrolyzing a compound represented by Chemical Formula 1:

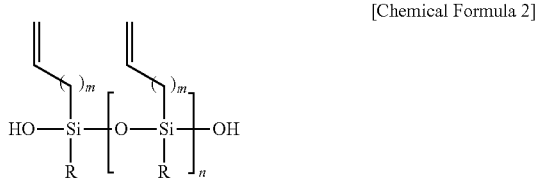

[Chemical Formula 2]

wherein R is alkyl or hydroxyl, m is an integer from 1 to 18 and n is an integer from 0 to 3.

The present invention also provides a method for preparing the terminal alkenylsilanepolyol derivative represented by Chemical Formula 2 by hydrolyzing a terminal alkenylsilane compound represented by Chemical Formula 1a at 0-40° C. using a 0.1-10 wt % acetic acid aqueous solution:

[Chemical Formula 1a]

wherein Y is methyl or OR', with R' being $C_{1-6}$ alkyl, R is methyl or hydroxyl and m is an integer from 1 to 18.

The concentration of the acetic acid aqueous solution may be 0.1-10 wt %, specifically 0.5-1.5 wt %. The volume of the acetic acid aqueous solution may be 70-200, specifically 90-120, based on 100 of the terminal alkenylsilane compound represented by Chemical Formula 2. The hydrolysis may be performed at 0-40° C., more specifically at 20-30° C.

Specifically, the alkenyl(alkoxy)silane compound represented by Chemical Formula 1a used in the present invention may be selected from allyltrimethoxysilane, allyltriethoxysilane, pentenyltrimethoxysilane, pentenyltriethoxysilane, hexenyltrimethoxysilane, hexenyltriethoxysilane, heptenyltrimethoxysilane, heptenyltriethoxysilane, octenyltritrimethoxysilane, octenyltriethoxysilane, allylmethyldimethoxysilane, allylmethyldiethoxysilane, pentenylmethyldimethoxysilane, pentenylmethyldiethoxysilane, hexenylmethyldimethoxysilane, hexenylmethyldiethoxysilane, heptenylmethyldimethoxysilane, heptenylmethyldiethoxysilane, octenylmethyldimethoxysilane, octenylmethyldiethoxysilane, octadecenyltrimethoxysilane, octadecenylethoxysilane, icosenyltrimethoxysilane and icosenyltriethoxysilane.

The present invention also provides surface-modified inorganic oxide particles whose surface is chemically modified using a solution of the alkenylsilane-terminated compound represented by Chemical Formula 2, which is obtained by hydrolyzing the terminal alkenylsilanepolyol compound represented by Chemical Formula 1a.

Accordingly, the present invention includes a method for preparing inorganic oxide particles surface-modified with terminal alkenyl groups, including: preparing a solution of the terminal alkenylsilanepolyol derivative represented by Chemical Formula 2 by hydrolyzing the alkenylsilane-terminated compound represented by Chemical Formula 1a; obtaining inorganic particles whose surface is coated with a molecular layer by adding the terminal alkenylsilane compound to inorganic particles dispersed in one or more solvent selected from alcohol and water and then evaporating the solvent; and dehydration condensing the inorganic oxide particles whose surface is coated with a molecular layer by heating.

Alternatively, the inorganic oxide particles may be modified at high temperature via a spraying process using the terminal alkenylsilanepolyol.

Specifically, the terminal alkenylsilanepolyol derivative represented by Chemical Formula 2 can be used for one or more inorganic oxide particles selected from silica, mica, talc, titanium oxide, zirconium oxide, tin oxide, zinc oxide, iron oxide and yttrium oxide.

The present invention also provides another method for preparing inorganic oxide particles surface-modified with terminal alkenyl groups, including preparing a suspension by mixing a terminal alkenylsilane compound represented by Chemical Formula 1a, inorganic oxide particles and an alcohol aqueous solution at pH 2.5-5.0, removing alcohol and water from the suspension by evaporation and performing dehydration condensation by heating.

EXAMPLES

The examples and experiments will now be described. The following examples and experiments are for illustrative purposes only and not intended to limit the scope of this invention.

Synthesis Example 1

Hydrolysis of allyltrimethoxysilane 1 mL of a 1 wt % acetic acid aqueous solution was added to a 50-mL flask. Allyltrimethoxysilane (1.0 g) was added with stirring and reaction was carried out at room temperature (20° C.) for 15 minutes. When the solution became clear, the stirring was stopped and the solvent was removed using a rotary evaporator to obtain 0.72 g (yield: 97%) of product. The structure of the product was identified by NMR spectroscopy (see FIG. 1).

Allylsilanetriol $^1$H NMR (THF-$d_8$) δ 1.44-1.58 (m, 2H, $CH_2Si$), 4.70-4.90 (m, 2H, $CH=CH_2$), 5.26 (s, 3H, SiOH), 5.76-5.93 (m, 1H, $CH_2=CH$).

By changing the reaction condition, 1,3-diallyldisiloxane-1,1,3,3-tetraol, a dimer of the allylsilanetriol, can be synthesized as main product. 0.55 g (yield: 80%) of 1,3-diallyldisiloxane-1,1,3,3-tetraol was obtained in the same manner by adding 1 mL of a 3 wt % acetic acid aqueous solution and 1.0 g of allyltrimethoxysilane and carrying out reaction. The structure of the product was identified by NMR spectroscopy.

1,3-Diallyldisiloxane-1,1,3,3-tetraol $^1$H NMR (THF-$d_8$) δ 1.45-1.60 (m, 4H, $CH_2Si$), 4.71-4.94 (m, 4H, $CH=CH_2$), 5.31 (s, 4H, SiOH), 5.77-5.94 (m, 2H, $CH_2=CH$).

Synthesis Example 2

Hydrolysis of octenyltrimethoxysilane 1 mL of a 1 wt % acetic acid aqueous solution was added to a 50-mL flask. Octenyltrimethoxysilane (1.0 g) was added with stirring and reaction was carried out at room temperature (20° C.) for 15 minutes. When the solution became clear, the stirring was stopped and the solvent was removed using a rotary evaporator to obtain 0.79 g (yield: 96%) of product. The structure of the product was identified by NMR spectroscopy.

7-Octenylsilanetriol $^1$H NMR (THF-d$_8$) δ 0.62-0.66 (br. t, 2H, SiCH$_2$), 1.27 (broad, 8H, CH$_2$), 2.00-2.04 (m, 2H, CH$_2$—CH=), 4.82-5.08 (m, 2H, CH$_2$=CH), 5.25 (s, 3H, SiOH), 5.58-6.00 (m, 1H, CH$_2$=CH).

By changing the reaction condition, 1,3-di(7-octenyl)disiloxane-1,1,3,3-tetraol, a dimer of the octenylsilanetriol, can be synthesized as main product. 0.60 g (yield: 78%) of 1,3-di(7-octenyl)disiloxane-1,1,3,3-tetraol was obtained in the same manner by adding 1 mL of a 3 wt % acetic acid aqueous solution and 1.0 g of 7-octenyltrimethoxysilane and carrying out reaction. The structure of the product was identified by NMR spectroscopy.

1,3-Di(7-octenyl)disiloxane-1,1,3,3-tetraol $^1$H NMR (THF-d$_8$) δ 0.62-0.65 (br. t, 4H, SiCH$_2$), 1.27 (broad, 16H, CH$_2$), 2.00-2.04 (m, 4H, CH$_2$—CH=), 4.81-5.07 (m, 4H, CH$_2$=CH), 5.25 (s, 6H, SiOH), 5.58-5.99 (m, 2H, CH$_2$=CH).

Test Example 1

Hydrolysis of alkenylalkoxysilane 100 parts by weight of a 1% acetic acid aqueous solution based on 100 parts by weight of an alkenylalkoxysilane compound was added to a container including the alkenylalkoxysilane compound. Thus prepared solution was stirred at 25° C. until all the hydrophobic alkoxy groups of the alkenylalkoxysilane compound were converted into hydrophilic hydroxyl groups to give a clear solution. Reaction time is shown in Table 1. The used organic alkoxysilane compounds were vinyltrimethoxysilane (VTMS), allyltrimethoxysilane (ATMS), 7-octenyltrimethoxysilane (OTMS) and (bicyclo[2.2.1]hept-5-en-2-yl)trimethoxysilane (BCHTMS).

TABLE 1

|   | Alkenylalkoxysilane compound | Reaction time |
|---|---|---|
| 1 | VTMS | 3 minutes |
| 2 | ATMS | 15 minutes |
| 3 | OTMS | 6 hours |
| 4 | BCHTMS | 1 day |

The hydrolysis time was measured depending on the alkenylalkoxysilane. The time required for the surface modification of silica is determined by the hydrolysis time.

Preparation of Functional Reinforcing Filler using alkenylsilanol Obtained by hydrolyzing alkenylalkoxysilane Compound Example 1

24.0 mmol (3.56 g) of vinyltrimethoxysilane (VTMS) was added to 3.56 g of a 1% acetic acid aqueous solution (pH ~3.5) in a 25-mL flask. After stirring for 3 minutes at room temperature, a transparent vinylsilanol solution was obtained. The hydrolyzed vinylsilanol solution was added to a slurry containing 60 g of silica (Z115GR, Rhodia Silica) and 150 g of methanol, and the mixture was stirred at room temperature for 10 minutes. Then, after evaporating the solvent and volatile materials using a rotary vacuum evaporator, residual solid particles were dehydration condensed in an oven at 130° C. for 8 hours to prepare silica (hydrophobic, highly dispersible functional reinforcing filler) surface-modified with the vinyl group.

Example 2

24.0 mmol (3.89 g) of allyltrimethoxysilane (ATMS) was added to 3.89 g of a 1% acetic acid aqueous solution (pH ~3.5) in a 25-mL flask. After stirring for 15 minutes at room temperature, a transparent allylsilanol solution was obtained. The hydrolyzed allylsilanol solution was added to a slurry containing 60 g of silica (Z115GR, Rhodia Silica) and 150 g of methanol, and the mixture was stirred at room temperature for 10 minutes. Then, after evaporating the solvent and volatile materials using a rotary vacuum evaporator, residual solid particles were dehydration condensed in an oven at 130° C. for 8 hours to prepare silica (hydrophobic, highly dispersible functional reinforcing filler) surface-modified with the allyl group.

Example 3

24.0 mmol (5.58 g) of 7-octenyltrimethoxysilane (OTMS) was added to 5.58 g of a 1% acetic acid aqueous solution (pH ~3.5) in a 25-mL flask. After stirring for 6 hours at room temperature, a transparent 7-octenylsilanol solution was obtained. The hydrolyzed 7-octenylsilanol solution was added to a slurry containing 60 g of silica (Z115GR, Rhodia Silica) and 150 g of methanol, and the mixture was stirred at room temperature for 10 minutes. Then, after evaporating the solvent and volatile materials using a rotary vacuum evaporator, residual solid particles were dehydration condensed in an oven at 130° C. for 8 hours to prepare silica (hydrophobic, highly dispersible functional reinforcing filler) surface-modified with the 7-octenyl group.

Example 4

24.0 mmol (5.14 g) of (bicyclo[2.2.1]hept-5-en-2-yl)trimethoxysilane (BCHTMS) was added to 3.56 g of a 1% acetic acid aqueous solution (pH ~3.5) in a 25-mL flask. After stirring for 24 hours at room temperature, a transparent (bicyclo[2.2.1]hept-5-en-2-yl)trisilanol solution was obtained. The hydrolyzed (bicyclo[2.2.1]hept-5-en-2-yl)trisilanol solution was added to a slurry containing 60 g of silica (Z115GR, Rhodia Silica) and 150 g of methanol, and the mixture was stirred at room temperature for 10 minutes. Then, after evaporating the solvent and volatile materials using a rotary vacuum evaporator, residual solid particles were dehydration condensed in an oven at 130° C. for 8 hours to prepare silica (hydrophobic, highly dispersible functional reinforcing filler) surface-modified with the bicyclo[2.2.1]hept-5-en-2-yl group.

Examples 5-6

Surface-modified silica (hydrophobic, highly dispersible functional reinforcing filler) was prepared in the same manner as in Example 2, except for using 36.0 mmol (5.91 g, Example 4) or 48.0 mmol (7.88 g, Example 5) of allyltrimethoxysilane.

Example 7

24.0 mmol (3.89 g) of allyltrimethoxysilane (ATMS) was added to 3.89 g of a 1% acetic acid aqueous solution (pH ~3.5) in a 25-mL flask. After stirring for 15 minutes at room temperature, a transparent allylsilanol solution was obtained. After adding 3 g of bis[(triethoxysilyl)propyl]tetrasulfide (TESPT) and 3 g of a 1% acetic acid aqueous solution to a slurry containing 60 g of silica (Z115GR, Rhodia Silica) and 150 g of methanol, the mixture was stirred at about 65° C. for 2 hours and then cooled to room temperature. Subsequently, after adding the hydrolyzed allylsilanol solution, the mixture was stirred at room temperature for 10 minutes. Then, after evaporating the solvent and volatile materials using a rotary vacuum evaporator, residual solid particles were dehydration condensed in an oven at 130° C. for 8 hours to prepare silica (hydrophobic, highly dispersible functional reinforcing filler) surface-modified with the allyl group and the bis [polyhydroxysilyl)propyl]tetrasulfide group.

Example 8

24.0 mmol (3.89 g) of allyltrimethoxysilane (ATMS) was added to 3.89 g of a 1% acetic acid aqueous solution (pH ~3.5) in a 25-mL flask. After stirring for 15 minutes at room temperature, a transparent allylsilanol solution was obtained. After adding 3 g of 3-mercaptopropyltrimethoxysilane (MPTMS) and 3 g of a 1% acetic acid aqueous solution to a slurry containing 60 g of silica (Z115GR, Rhodia Silica) and 150 g of methanol, the mixture was stirred at about 65° C. for 2 hours and then cooled to room temperature. Subsequently, after adding the hydrolyzed allylsilanol solution, the mixture was stirred at room temperature for 10 minutes. Then, after evaporating the solvent and volatile materials using a rotary vacuum evaporator, residual solid particles were dehydration condensed in an oven at 130° C. for 8 hours to prepare silica (hydrophobic, highly dispersible functional reinforcing filler) surface-modified with the allyl group and the 3-mercaptopropyl group.

Simultaneous Preparation of alkenylsilanol and Functional Reinforcing Filler

Example 9

A suspension including 60 g of silica (Z115GR, Rhodia Silica), 150 g of methanol, 3.89 g of allyltrimethoxysilane and 3.89 g of a 1% acetic acid aqueous solution was stirred at room temperature for 10 minutes. Then, after evaporating volatile materials using a rotary vacuum evaporator, residual solid particles were heated in an oven at 130° C. for 8 hours to prepare surface-modified silica (functional reinforcing filler).

Example 10

Surface Modification of Zinc Oxide Using allylsilanepolyol 24.0 mmol (3.89 g) of allyltrimethoxysilane (ATMS) was added to 3.89 g of a 1% acetic acid aqueous solution (pH ~3.5) in a 25-mL flask. After stirring for 15 minutes at room temperature, a transparent solution was obtained. The solution of hydrolyzed allylsilanepolyol prepared above was added to a slurry-type mixture of zinc oxide (60 g) and methanol (150 g) and stirred at room temperature for 10 minutes. Subsequently, after evaporating the solvent and volatile substances using a vacuum rotary evaporator, the remaining solid particles were subjected to dehydration condensation for 8 hours in an oven at 130° C. to obtain zinc oxide surface-modified with allyl groups.

Example 11

Surface Modification of Titanium Oxide Using allylsilanepolyol 24.0 mmol (3.89 g) of allyltrimethoxysilane (ATMS) was added to 3.89 g of a 1% acetic acid aqueous solution (pH ~3.5) in a 25-mL flask. After stirring for 15 minutes at room temperature, a transparent solution was obtained. The solution of hydrolyzed allylsilanepolyol prepared above was added to a slurry-type mixture of titanium oxide (60 g) and methanol (150 g) and stirred at room temperature for 10 minutes. Subsequently, after evaporating the solvent and volatile substances using a vacuum rotary evaporator, the remaining solid particles were subjected to dehydration condensation for 8 hours in an oven at 130° C. to obtain titanium oxide surface-modified with allyl groups.

Preparation of Rubber Sample Using Hydrophobic, Highly Dispersible Functional Reinforcing Filler

Preparation Example

[Standard Mixing Protocol]

Test samples of rubber compositions including the silica prepared in Examples t were prepared according to the standard mixing protocol shown in Table 2. The components were mixed using a Haake mixer (Rheocord 9000) at 140° C. to prepare the test samples.

TABLE 2

|  | Amount (parts by weight) | Adding time (min) | Rotor speed (rpm) |
| --- | --- | --- | --- |
| First pass |  |  |  |
| SSBR[(1)] | 100 | 0 | 60 |
| BR[(2)] | 30 | 0 |  |
| Filler | 70 | 2 |  |
| Zinc oxide[(3)] | 3 | 0.5 |  |
| Stearic acid[(4)] | 2 | 0.5 |  |
| Wax[(5)] | 2 | 0.5 |  |
| 3C[(6)] | 3 | 0.5 |  |
| Sweep |  | 3 |  |
| Second pass |  |  |  |
| Products of first pass | All | 7 | 15.3 |
| Sulfur[(7)] | 1.7 |  |  |
| CZ[(8)] | 2 |  |  |
| DPG[(9)] | 0.6 |  |  |

[(1)]SSBR: solution styrene-butadiene rubber (Sol6450SL, Kumho Petrochemical)
[(2)]BR: butadiene rubber (KBR-01, Kumho Petrochemical)
[(3)]Zinc oxide: ZnO#2 (Hanil Zinc)
[(4)]Stearic acid: STAcid (LG Chem)
[(5)]Wax: P-Wax (Nippon Seiro)
[(6)]N-isopropyl-N'-phenylenediamine (3C, Samwon)
[(7)]Sulfur: SP-325 (Miwon Commercial)
[(8)]CZ: N-cyclohexylbenzothoazylsulfenamide (SAMACCZ, Samwon)
[(9)]DPG: diphenylguanidine

Preparation Example 1

A rubber sample was prepared using the hydrophobic, highly dispersible functional reinforcing filler prepared in Example 1 according to the standard mixing protocol of Table 2. The composition of the rubber sample is shown in Table 3.

Preparation Example 2

A rubber sample was prepared using the hydrophobic, highly dispersible functional reinforcing filler prepared in Example 2 according to the standard mixing protocol of Table 2. The composition of the rubber sample is shown in Table 3.

Preparation Example 3

A rubber sample was prepared using the hydrophobic, highly dispersible functional reinforcing filler prepared in Example 3 according to the standard mixing protocol of Table 2. The composition of the rubber sample is shown in Table 3.

Preparation Example 4

A rubber sample was prepared using the hydrophobic, highly dispersible functional reinforcing filler prepared in Example 4 according to the standard mixing protocol of Table 2. The composition of the rubber sample is shown in Table 3.

Preparation Examples 5-6

Rubber samples were prepared using the hydrophobic, highly dispersible functional reinforcing fillers prepared in Examples 5-6 according to the standard mixing protocol of Table 2. The composition of the rubber sample is shown in Table 3.

Preparation Examples 7-8

Rubber samples were prepared using the hydrophobic, highly dispersible functional reinforcing fillers prepared in Example 2 according to the standard mixing protocol of Table 2. The composition of the rubber sample is shown in Table 3.

Preparation Example 9

A rubber sample was prepared using the hydrophobic, highly dispersible functional reinforcing filler prepared in Example 7 according to the standard mixing protocol of Table 2. The composition of the rubber sample is shown in Table 3.

Preparation Example 10

A rubber sample was prepared using the hydrophobic, highly dispersible functional reinforcing filler prepared in Example 8 according to the standard mixing protocol of Table 2. The composition of the rubber sample is shown in Table 3.

Preparation Example 11

A rubber sample was prepared using the hydrophobic, highly dispersible functional reinforcing filler prepared in Example 9 according to the standard mixing protocol of Table 2. The composition of the rubber sample is shown in Table 3.

Comparative Preparation Examples 1-6

Rubber samples were prepared by simply mixing sulfur-free allyltrimethoxysilane (ATMS) with non-surface-treated silica at 140° C. (Comparative Preparation Examples 1-2), using a sulfur-free coupling agent 3-mercaptopropyltrimethoxysilane (MPTMS) and non-surface-treated silica (Comparative Preparation Examples 3-4), or using a coupling agent bis[(triethoxysilyl)propyl]tetrasulfide (TESPT) and non-surface-treated silica (Comparative Preparation Examples 5-6). The composition of the rubber samples is shown in Table 3.

TABLE 3

| | | Preparation Examples (parts by weight) | | | | Comparative Preparation Examples (parts by weight) | | | | | |
|---|---|---|---|---|---|---|---|---|---|---|---|
| | | 1-6 | 7 | 8 | 9-11 | 1 | 2 | 3 | 4 | 5 | 6 |
| | SSBR | 100 | 100 | 100 | 100 | 100 | 100 | 100 | 100 | 100 | 100 |
| | BR | 30 | 30 | 30 | 30 | 30 | 30 | 30 | 30 | 30 | 30 |
| Filler | Surface-modified silica | 70 | 70 | 70 | 70 | — | — | — | — | — | — |
| | Non-surface-modified silica[1] | — | — | — | — | 65.4 | 65.4 | 64.1 | 64.1 | 64.4 | 64.4 |
| | Coupling agent | — | — | — | — | 4.6[2] | 4.6[2] | 5.9[3] | 5.9[3] | 5.6[4] | 5.6[4] |
| | Zinc oxide | 3 | 3 | 3 | 3 | 3 | 3 | 3 | 3 | 3 | 3 |
| | Stearic acid | 2 | 2 | 2 | 2 | 2 | 2 | 2 | 2 | 2 | 2 |
| | Wax | 2 | 2 | 2 | 2 | 2 | 2 | 2 | 2 | 2 | 2 |
| | 3C | 3 | 3 | 3 | 3 | 3 | 3 | 3 | 3 | 3 | 3 |
| | Sulfur | 1.7 | 3.0 | 5.0 | 1.7 | 1.7 | 3.0 | 1.7 | 3.0 | 1.7 | 3.0 |
| | CZ | 2 | 2 | 2 | 2 | 2 | 2 | 2 | 2 | 2 | 2 |
| | DPG | 0.6 | 0.6 | 0.6 | 0.6 | 0.6 | 0.6 | 0.6 | 0.6 | 0.6 | 0.6 |

[1]Silica: Z115GR (Rhodia Silica)
[2]ATMS: TCD
[3]MPTMS: TCD
[4]TESPT: Si69 (Evonik)

Test Example 2

Physical Properties of Rubber Sample

Physical properties of the rubber samples prepared in Preparation Examples 1-10 and Comparative Preparation Examples 1-6 were measured. The result is shown in Table 4.

The samples were cured for the T90 time according to ASTM D-2094, i.e. the time during which 90% of vulcanization is completed, plus additional 5 minutes at 150° C. under a pressure of 2,000 lb/int. Physical properties of the samples were measured using the test method A according to ASTM D412-98a. Extension rate, tensile stress and modulus were measured using the Lloyd instruments (LRX Plus, Ametek, Inc.). In Table 4, TS2 indicates the scorch time, or the initial curing time, of rubber.

ration Examples 3-6, wherein sulfur-containing MPTMS or TESPT was used as the coupling agent, further addition of sulfur did not lead to improved physical properties.

TABLE 4

|  | Preparation Examples | | | | | | | | | | | Comparative Preparation Examples | | | | | |
|---|---|---|---|---|---|---|---|---|---|---|---|---|---|---|---|---|---|
|  | 1 | 2 | 3 | 4 | 5 | 6 | 7 | 8 | 9 | 10 | 11 | 1 | 2 | 3 | 4 | 5 | 6 |
| Scorch time (TS2) | 15.1 | 17.0 | 16.6 | 16.2 | 16.5 | 14.1 | 16.8 | 13.7 | 12.2 | 10.9 | 16.9 | 14.1 | 14.8 | 1.1 | 1.3 | 7.5 | 5.5 |
| Vulcanization time (T90) | 18.9 | 21.8 | 20.1 | 20.0 | 22.6 | 17.4 | 22.5 | 32.0 | 16.4 | 15.5 | 21.0 | 16.7 | 23.4 | 7.9 | 8.5 | 13.1 | 13.1 |
| Tensile strength (MPa) | 17.3 | 17.9 | 17.3 | 17.5 | 18.0 | 18.2 | 19.3 | 19.6 | 19.5 | 18.9 | 17.8 | 16.9 | 17.2 | 11.0 | 10.8 | 15.9 | 15.0 |
| 300% modulus (MPa) | 13.9 | 15.1 | 14.1 | 14.2 | 16.1 | 17.3 | 17.8 | 18.2 | 18.1 | 17.9 | 13.9 | 15.5 | 16.2 | 12.3 | 11.4 | 12.6 | 12.2 |

As seen from Table 4, the rubber samples prepared in Preparation Examples 1-4 using the silica surface-modified with the alkenylalkoxysilane exhibited longer scorch time and vulcanization time, and hence better processability and higher tensile strength and 300% modulus, than the rubber samples prepared in Comparative Preparation Examples 3-6 using the sulfur-containing silane coupling agent. Among them, the rubber sample prepared in Preparation Example 2 using the silica surface-modified with allyltrimethoxysilane showed the best result as a reinforcing filler with satisfactory scorch time, vulcanization time, tensile strength and 300% modulus. Comparison of Preparation Examples 5 and 6 reveals that tensile strength and 300% modulus can be improved by increasing the amount of allyltrimethoxysilane. Preparation Examples 7 and 8 show that the tensile strength and modulus can be significantly improved by adding sulfur to Preparation Example 2, without having to add the expensive coupling agent as in Preparation Examples 5-6. This is because the sulfur that has been uniformly dispersed in the rubber mixture reacts with the allyl group of the coupling agent, thereby facilitating the rubber-coupling agent-silica bonding. Also, it was identified through Preparation Examples 9 and 10 that physical properties can be greatly improved by modifying the surface using the sulfur-containing TESPT or MPTMS. In Preparation Example 11, wherein allylsilanepolyol and silica were surface-modified simultaneously using allyltrimethoxysilane, a similar result was obtained as in Preparation Example 2.

Preparation Example 2 wherein the silica surface-modified with allyltrimethoxysilane was used showed better physical properties as compared to Comparative Preparation Example 1 wherein silane and sulfur were simply mixed with the same amount. Comparative Preparation Example 1 showed slightly improved physical properties as compared to Comparative Preparation Example 2, revealing that the addition of sulfur when mixing allyltrimethoxysilane with silica rubber can provide improved physical properties. In Comparative Preparation Examples 3-6, wherein sulfur-containing MPTMS or TESPT was used as the coupling agent, further addition of sulfur did not lead to improved physical properties.

Test Example 3

Dynamic Properties of Rubber Sample

Dynamic properties of the rubber samples prepared in Preparation Examples and Comparative Preparation Examples were measured. The result is shown in Tables 5 and 6.

TABLE 5

|  | Preparation Examples | | | | | | | | | | |
|---|---|---|---|---|---|---|---|---|---|---|---|
|  | 1 | 2 | 3 | 4 | 5 | 6 | 7 | 8 | 9 | 10 | 11 |
| Tan δ (0° C.) | 0.199 | 0.205 | 0.203 | 0.200 | 0.196 | 0.206 | 0.215 | 0.217 | 0.207 | 0.207 | 0.203 |
| Tan δ (60° C.) | 0.075 | 0.069 | 0.077 | 0.075 | 0.060 | 0.051 | 0.053 | 0.050 | 0.049 | 0.052 | 0.068 |

TABLE 6

|  | Comparative Preparation Examples | | | | | |
|---|---|---|---|---|---|---|
|  | 1 | 2 | 3 | 4 | 5 | 6 |
| Tan δ (0° C.) | 0.205 | 0.205 | 0.155 | 0.165 | 0.162 | 0.187 |
| Tan δ (60° C.) | 0.069 | 0.061 | 0.066 | 0.061 | 0.059 | 0.056 |

Since Preparation Examples show higher tan δ (0° C.) and lower tan δ (60° C.) values as compared to Comparative Preparation Examples, improvement in braking performance and low rotational resistance are expected. Especially, Preparation Examples 7-10 exhibited high tan δ (0° C.) values as well as low tan δ (60° C.) values. This may be due to the addition of sulfur or the sulfur-containing coupling agent to the rubber mixture of silica surface-modified with allyltrimethoxysilane.

Since the functional reinforcing filler of the present invention has a functional group having a double bond, it has good reactivity for styrene-butadiene rubber and sulfur. Thus, when used as a functional reinforcing filler in the manufacture of rubber, it allows improvement of physical properties through adjustment of the addition amount of sulfur without additional use of the coupling agent. In addition, because of superior hydrolysis reactivity, the problem of alcohol can be solved and a rubber mixture with long scorch time can be prepared. In particular, when the functional reinforcing filler of the present invention is used in the manufacture of tires, improvement in modulus, tensile strength, rotational resistance and wet traction performance can be expected.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. Inorganic oxide particles surface-modified with a solution of a terminal alkenylsiloxanepolyol represented by Chemical Formula 2:

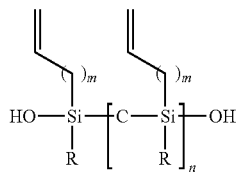

wherein R is alkyl or hydroxyl, m is an integer from 1 to 18 and n is an integer from 0 to 3, wherein the alkenylsiloxanepolyol is formed by hydrolysis from a terminal alkenylalkoxysilane compound, and wherein the surface modified inorganic oxide particles are formed from the inorganic oxide particles and the terminal alkenylalkoxysilane compound in an amount of between 100:15 and 100:3 parts by weight.

2. The inorganic oxide particles according to claim 1, wherein the inorganic particles are one or more selected from silica, mica, talc, titanium oxide, zirconium oxide, tin oxide, zinc oxide, iron oxide and yttrium oxide and have an average particle diameter of 5 nm to 100 μm.

3. The inorganic oxide particles according to claim 1, wherein the inorganic particles have a BET surface area of 50-1,000 m²/g.

4. The inorganic oxide particles according to claim 1, wherein the hydrolysis is performed at pH 2.5-5.0.

5. The inorganic oxide particles according to claim 1, wherein the inorganic oxide particles are further modified with a coupling agent selected from bis[(trimethoxysilyl)propyl]tetrasulfide (TMSPT), bis[(triethoxysilyl)propyl]tetrasulfide (TESPT), 3-mercaptopropyltrimethoxysilane (MPTMS) and 3-mercaptopropyltriethoxysilane (MPTES).

6. The inorganic oxide particles according to claim 1, wherein the terminal alkenylalkoxysilane compound is allyltrimethoxysilane.

7. A filler composition comprising (a) inorganic oxide particles surface-modified with a solution of a terminal alkenylsiloxanepolyol represented by Chemical Formula 2:

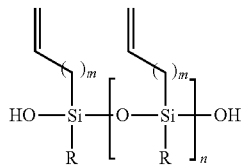

wherein R is alkyl or hydroxyl, m is an integer from 1 to 18 and n is an integer from 0 to 3; and (b) sulfur.

8. A rubber composition comprising (a) an elastomer, and (b) a filler comprising inorganic oxide particles surface-modified with a solution of a terminal alkenylsiloxanepolyol represented by Chemical Formula 2:

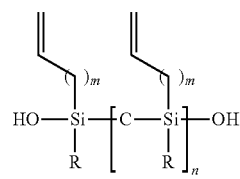

wherein R is alkyl or hydroxyl, m is an integer from 1 to 18 and n is an integer from 0 to 3, wherein the filler is present in an amount of 10 to 200 parts by weight based on 100 parts by weight of the elastomer.

9. The composition according to claim 8, wherein the elastomer comprises at least one selected from the group consisting of (i) a homopolymer comprising conjugated diene monomers; and (ii) a copolymer comprising a conjugated diene monomer, a monovinyl aromatic monomer and a triene monomer, and wherein the alkenylsiloxanepolyol is formed by hydrolysis from a terminal alkenylalkoxysilane compound, and wherein the surface modified inorganic oxide particles are formed from the inorganic oxide particles and the terminal alkenylalkoxysilane compound in an amount of between 100:15 and 100:3 parts by weight.

10. The composition according to claim 8 comprising an organic rubber.

11. The composition according to claim 8, wherein the filler further comprises sulfur.

* * * * *